United States Patent
Venturini et al.

(10) Patent No.: US 6,537,275 B2
(45) Date of Patent: Mar. 25, 2003

(54) SECURING COMPONENT FOR A RING FIXATOR USED IN ORTHOPAEDIC SURGERY

(75) Inventors: Daniele Venturini, Verona (IT); Michele Coati, Verona (IT); Graziano Rossi, Verona (IT)

(73) Assignee: Orthodix S.r.l., Bussolengo (IT)

( * ) Notice: Subject to any disclaimer, the term of this patent is extended or adjusted under 35 U.S.C. 154(b) by 0 days.

(21) Appl. No.: 09/847,718

(22) Filed: May 2, 2001

(65) Prior Publication Data

US 2001/0049526 A1 Dec. 6, 2001

(30) Foreign Application Priority Data

May 9, 2000 (EP) .............................. 00830340

(51) Int. Cl.$^7$ ............................................. A61B 17/56
(52) U.S. Cl. ...................................................... 606/56
(58) Field of Search ............................. 606/53, 54, 56, 606/59, 57, 58

(56) References Cited

U.S. PATENT DOCUMENTS

| | | | | |
|---|---|---|---|---|
| 4,628,919 A | * | 12/1986 | Clyburn | 128/92 |
| 4,714,076 A | * | 12/1987 | Comte et al. | 128/92 ZW |
| 6,053,915 A | * | 4/2000 | Bruchmann | 606/54 |
| 6,129,727 A | * | 10/2000 | Austin et al. | 606/56 |
| 6,217,577 B1 | * | 4/2001 | Hofmann | 606/57 |

FOREIGN PATENT DOCUMENTS

FR    2595045 A1    9/1987

OTHER PUBLICATIONS

"Monticelli Spinelli External Fixation System", Jacquet Orthopedie S.A., Geneva, Switzerland (1990).

* cited by examiner

*Primary Examiner*—Eduardo C. Robert
(74) *Attorney, Agent, or Firm*—Leydig, Voit & Mayer, Ltd.

(57) ABSTRACT

The invention relates to a clamp element for external fixator apparatuses of the rod and ring type used for stabilizing bone fractures in orthopedic surgery; a clamp connector secures at least one of the bone fragment stretching wires and the bone screws to the rings. The invention comprises a swivel joint comprising a first part and a second part associated with each other around a common pivot axis, each part being formed with at least one hole of a predetermined diameter for clamping the stretching wire or the bone screw therein. Also provided on each of the parts are clamping mechanisms for attaching to a rod or to a ring of the fixator device. The clamping mechanisms are used for clamping the stretching wire or the bone screw in the part of the swivel joint which is not connected to the rod or to the ring.

9 Claims, 1 Drawing Sheet

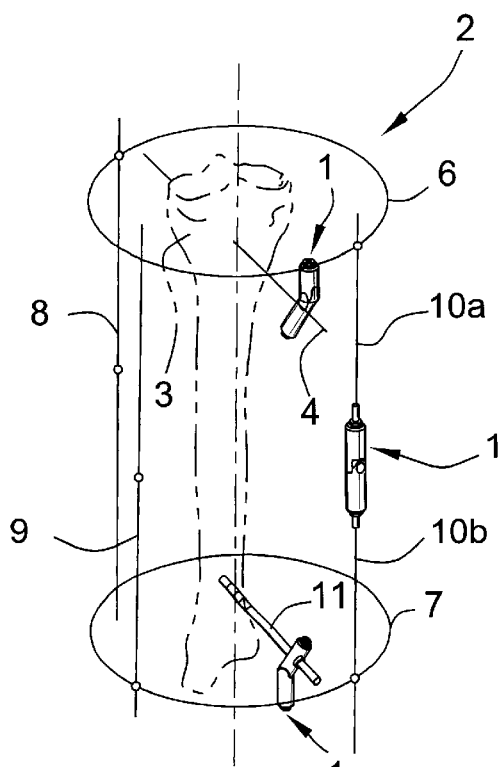
FIG. 1
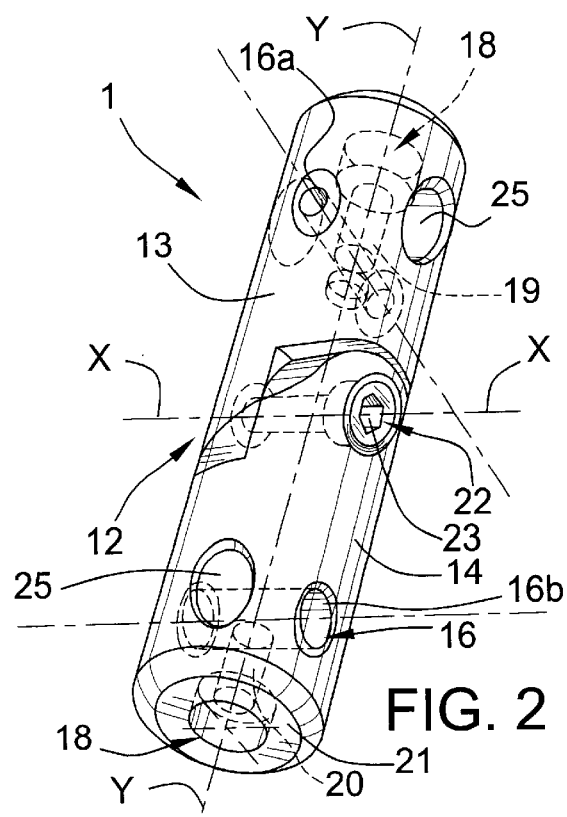
FIG. 2
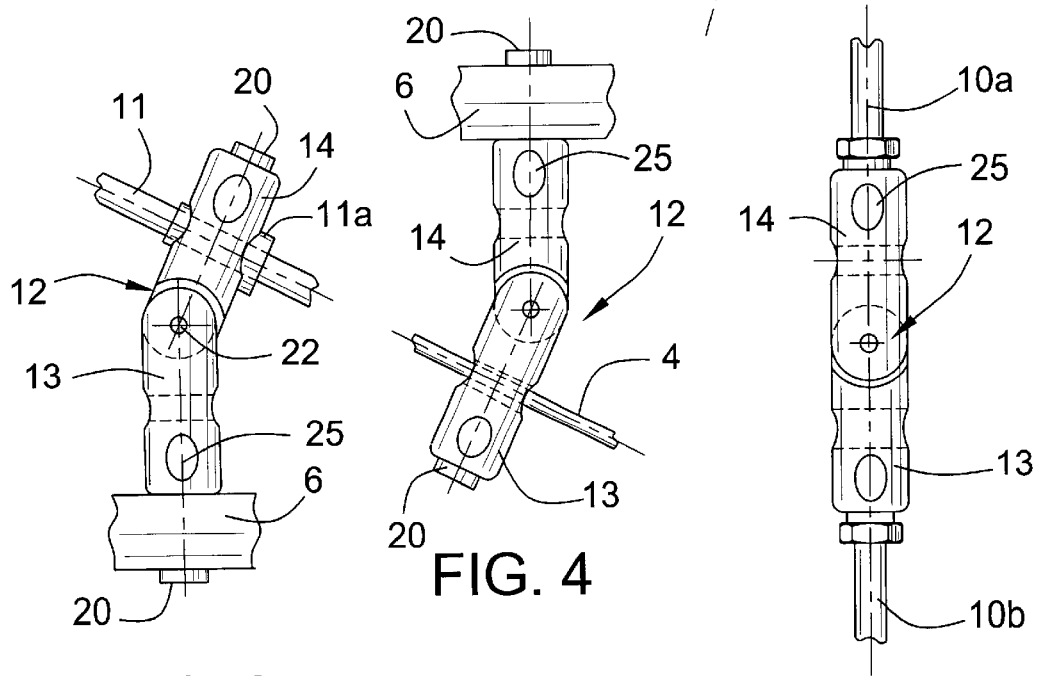
FIG. 3
FIG. 4
FIG. 5

SECURING COMPONENT FOR A RING FIXATOR USED IN ORTHOPAEDIC SURGERY

FIELD OF THE INVENTION

This invention broadly relates to an element for an external ring fixator used for stabilizing bone fractures in orthopedic surgery.

More particularly, the invention relates to a clamp element for external fixators of the rod and ring type used for stabilizing bone fractures in orthopedic surgery; such clamp element secures at least one of the bone fragment stretching wires and the bone screws to one of the fixator rings.

As it is known in this technical field, external fixators are modular apparatuses, comprising a plurality of component parts, which can be assembled with each other into a variety of different configurations.

PRIOR ART

A typical example of this kind of fixator apparatuses is the Ilizarov system, wherein bone fragment fixing rings can be assembled with each other by means of extendible connecting tie rods or plates.

Such fixator apparatuses allow complex bone fractures to be recomposed, e.g. in the case the bone end of a limb has been splintered and one or more bone fragments happen to be dislocated from said bone end.

In such cases, stretching wires are suitably used; such wires have an end threading a hole drilled in the bone fragment, and bent over it in order to hold it in place. The opposite end of the stretching wire is made fast to one of the rings and here held.

In the Ilizarov system, the means used for securing the end of the stretching wire to the rings consists of simple bolts, inserted in holes made in the rings, and their associated nuts. Alternatively, special bolts having a hole drilled crossly to their threaded shank may be used; the hole receives the end of the stretching wire which is then clamped on the ring by means of a nut.

In some cases, for example when the bone fragment to recompose occurs at an intermediate location of the limb, the end of the stretching wire must be fastened at an angle to the plane containing the ring. In such cases, articulated clamp elements are used, which usually comprise a first portion secured to the ring and a second portion inclined to the plane of the ring and having clamping means of the stretching wire end.

Furthermore, different conditions of the bone fracture can require that a bone screw be used having a threaded end engaged in the bone cortex, and having an opposite screw-handling to be end secured to one of the rings. Here again, a respective different clamp element must be provided.

Thus, a multiplicity of clamp elements—differing from one another by their type, function and assembling method—must be made available, depending on whether the stretching wire for bone fragments or a bone screw is to be secured to the ring. This obviously involves higher manufacturing cost, since large volume production methods cannot be applied.

In addition, the provision of a range of different clamp elements implies the disadvantage for the orthopedic surgeon, who has always the duty to select the most suitable element to complete the installation of the fixator device. This selection requirement works against the necessity to have the fixator apparatus assembling and setting operations completed within the shortest possible time.

The underlying technical problem of this invention is to contrive a clamp element, particularly to be used in external fixator apparatuses of the rod and ring type, with such structural and functional features as to allow its universal application in a variety of assembling situations and conditions, and accordingly, its manufacture in large volumes. The limitations and drawbacks of the solutions presently proposed in the prior art would thus be overcome.

SUMMARY OF THE INVENTION

The resolutive idea of this invention is to arrange for a clamp element to comprise a pair of portions articulated with each other by a pivotal connection, each of such portions being interchangeably usable to secure the clamp element either to one of the fixator apparatus rings, or to a bone fragment stretching wire, or to a bone screw.

Based on this resolutive idea, this invention provides a clamp element as previously indicated and defined in the characterizing portion of claim 1.

The features and advantages of the clamp element according to the invention will be apparent by reading the following description of a preferred embodiment thereof, given by way of non-limitative example with reference to the accompanying drawings.

In the drawings:

BRIEF DESCRIPTION OF THE DRAWINGS.

FIG. 1 shows a perspective and schematic view of an external fixator apparatus of the ring type for use in orthopedic surgery, which fixator apparatus incorporates at least one clamp element according to the invention.

FIG. 2 shows a perspective view of a clamp element formed according to the invention;

FIG. 3 is a side view of the clamp element in FIG. 2, shown in a first condition of its use.

FIG. 4 is a side view of the clamp element in FIG. 2, shown in a second condition of its use.

FIG. 5 is a side view of the clamp element in FIG. 2, shown in a third condition of its use.

DETAILED DESCRIPTION

Referring to the enclosed drawings, a clamp element for external fixator apparatuses 2, e.g. fixators of the rod and the ring type for stabilizing bone fractures in orthopedic surgery, is at 1 inclusively and schematically shown.

Fixator apparatuses of the above type are usually applied to the outside of a limb which has been injured by a bone fracture.

A rod and ring type of fixator apparatus 2 includes at least a pair of rings, e.g. a proximal ring 6 and a distal ring 7, as well as tie rods 8, 9, 10 for connecting the rings 6 and 7 to each other.

Advantageously, a clamp element 1 according to this invention can be connected to either of said rings 6, 7 to secure at least one of the stretching wires 4 of a bone fragment 3 and the bone screw 11.

More particularly, the clamp element 1 comprises a swivel joint 12 comprising a first 13 and a second 14 parts associated with each other around a common pivot axis x-x. The parts 13, 14 are both formed with at least one hole 16 of a predetermined diameter for securing the stretching wire 4 or the bone screw 11. Specifically, the first part 13 is formed with a hole 16a having a diameter of about 3 mm for receiving the stretching wire 4, and the second part 14 is formed with a hole 16b having a diameter of about 6 mm for receiving the bone screw 11 and an optional takeup bush 11a.

In all cases, the diameter of the cross hole 16 in one of said parts is greater than the diameter of the cross hole 16 in the other part of said parts.

Also, the parts 13, 14 both include a means 18 of clamping to a rod 8, 9, 10 or a ring 6, 7 of said fixator apparatus.

Advantageously, the above-said clamping means 18 is also used for securing the stretching wire 4 or the bone screw 11 to the portion of the swivel joint 12, unconnected to the rod or to the ring.

Specifically, the clamping means 18 comprises a threaded seat 19 formed in one end of each of said parts 13, 14 for receiving a clamp screw 20, preferably of the Allen type.

Each said parts 13, 14 have an elongate cylindrical body, and the threaded seat 19 is formed in a free end 21 of the cylindrical body coaxially to the axis y-y of the latter.

The swivel joint 12 is basically a toggle joint, and includes a means 22 of stopping the pivotal angular rotation at a predetermined angular position around the common pivot axis x-x of the parts 13, 14.

In particular, the stopping means 22 comprises a grub-screw 23 extending coaxially to the pivot axis and adapted for manual operation using a suitable wrench.

It should be noted that the holes 16a and 16b in said first and second parts, 13 and 14, extend perpendicularly to the pivot axis x-x.

A threaded hole can be provided in the cylindrical body of each of the parts 13, 14, along a transverse direction to the seat 19 of said clamping means 18, for receiving a grub-screw operated to prevent the clamp screw 20 from turning.

For the sake of completeness, it should be added that the clamp element of this invention is made of a transparent material to X-radiation, such as a plastic matrix of polyetherketone. Also, the cylindrical body of each of said parts 13, 14 is formed laterally with a gripping impression 25 which essentially comprises a pair of parallel flats 24 provided on opposite sides of the axis y-y of the cylindrical body.

These gripping impressions 25 lie close to the free end 21 of each part, and make the handling of the clamp element easy, with or without the aid of a tool.

An explanation of how the clamp element of this invention can be used in an external fixator apparatus of the rod and the ring type, schematically shown in FIG. 3 will be given next, preceded by a brief review of the construction of a ring type fixator apparatus.

The rings 6 and 7 of the fixator 2 are superposed with a given distance apart, and held in place by the tie rods 8, 9 and 10. A respective end of the fractured limb is secured to each ring 6, 7, e.g. using suitable wires 4 for stretching bone fragments, or the bone screw 11.

The tie rods 8, 9 and 10 substantially extend along parallel directions. Two, 8 and 10, of the three rods 8, 9 and 10 are usually placed in diametrically opposite positions, while the third rod 9 is placed at 90°.

Each tie rod is threaded, and fastened to each ring by means of a nut and locknut.

The bone fragment stretching wire 4 is to be secured to one of the rings, 6 or 7, the operation being easily carried out thanks to the clamp element 1. For this purpose, the element 1 is fastened to the ring by the clamping screw 20, which screw engages in the threaded seat 19 of one of the parts 13, 14—specifically part 14 formed with the larger diameter hole 16b, as shown in FIG. 4—of the swivel joint 12 through one of a number of holes provided in the ring 6 or 7.

The stretching wire 4 is threaded through the hole 16a of the part 13 of the swivel joint 12 which is not fastened to the ring, and clamped therein by means of the screw 20 engaging in the corresponding threaded seat 19 at the free end of the part 13.

The angular setting of the swivel joint 12, that is the spatial lay of the part 13 relative to the part 14 fastened to the ring, is regulated by acting on the stop means 22 of the joint toggle.

In case a bone screw 11 is to be secured, instead of a stretching wire 4, it is enough to mount the clamp element 1 on the ring 6 or 7 the other way around according to what has been previously described, that is with the part 13 having the smaller diameter hole fastened to the ring and the other part 14 clamped to the bone screw, as shown in FIG. 3.

The clamp connector 1 can also be used according to a further connecting arrangement. In a preferred embodiment of the fixator device 2, at least one 10 of the tie rods 8, 9, or 10 comprises two rod sections, namely an upper rod section 10a and a lower rod section 10b, both substantially having the same length.

Advantageously, the rod sections 10a, 10b can be swivel connected together by means of the clamp element 1 of this invention. Each section can be engaged into a respective threaded seat 19 of each corresponding joint parts 13, 14.

Thus, the swivel joint 12 will locate approximately in the middle of the tie rod made up of the pair of sections, and enable adjustment of the relative inclination angle of the sections to suit the mutual setting of the rings 6 and 7.

In essence, with the clamp element 1 of this invention constructed as described hereinabove, the clamping of the stretching wire 4 or the bone screw 11 can be adjusted as desired both in position on one of the rings 6, 7 and in inclination to the plane of the ring.

The main advantage of the clamp element according to this invention is represented by its universal utility under different conditions of clamping either stretching wires, or bone screws, and rod sections connecting the rings.

A further advantage is the ease of assembly and operation of the clamp element, which can now be handily used by unskilled staff.

A further advantage is that the clamp element of this invention can be manufactured in very large volumes at reasonable costs.

What is claimed is:

1. A clamp element for securing at least one bone fragment stretching wire or at least one bone screw to a fixator ring of an external fixator apparatus having a rod and ring, the fixator apparatus used for stabilizing fractures in orthopedic surgery, said clamp element comprising
a first part and a second part associated with each other at a swivel joint, each part comprising an elongated cylindrical body, said elongated cylindrical body comprising
at least one hole of a predetermined diameter for clamping the stretching wire or the bone screw therein,
a free end,
a threaded seat formed in said free end of each of the elongated bodies, each said threaded seat being co-axial with the respective elongated body, and a nut or screw adapted to engage the rod or ring to clamp the clamp element to the rod or the ring.

2. The element, according to claim 1, wherein the swivel joint is a hinge defining a common pivot axis, and said first and second parts being rotatably disposed around the common pivot axis of said hinge.

3. The element according to claim 1, wherein said swivel joint comprises means to stop rotation of said first and second parts around said common pivot axis.

4. The element according to claim 2, wherein the holes in said first and second parts extend perpendicularly to the common pivot axis.

5. The element according to claim 1, wherein said threaded seat communicates with said hole.

6. The element according to claim 1, which is formed with a hole extending transversely to said seat for engagement of a grubscrew arranged to prevent said nut or screw from turning.

7. The element according to claim 1, wherein the holes in said parts have different diameters.

8. The element according to claim 1, further comprising a gripping impression which is formed laterally on at least one of said elongated cylindrical bodies.

9. The element according to claim 1, which is made of a material transparent to X-radiation.

* * * * *